United States Patent [19]

Dahms

[11] Patent Number: 4,725,552

[45] Date of Patent: Feb. 16, 1988

[54] KARL FISCHER REAGENT AND ITS USE

[76] Inventor: Harald Dahms, 472 Madison Ave., Toms River, N.J. 08753

[21] Appl. No.: 612,269

[22] Filed: May 21, 1984

[51] Int. Cl.$^4$ .............................................. G01N 33/18
[52] U.S. Cl. ...................................... 436/42; 204/1 T
[58] Field of Search ..................................... 436/39–42; 204/1 T

[56] References Cited

U.S. PATENT DOCUMENTS

| | | | |
|---|---|---|---|
| 2,780,601 | 2/1957 | Blomgren et al. | 436/42 |
| 2,967,155 | 1/1961 | Blomgrene et al. | 436/42 |
| 4,354,853 | 10/1982 | Dahms | 204/1 T |
| 4,368,105 | 1/1983 | Muroi et al. | 436/42 |
| 4,378,972 | 4/1983 | Scholz | 436/42 |
| 4,429,048 | 1/1984 | Scholz | 436/42 |

Primary Examiner—Arnold Turk

[57] ABSTRACT

Karl Fischer reagents of the two-component type are described which eliminate problems such as inaccurate results and false end-points during titrations to determine the water content of a sample. The two-component reagent includes a vessel solution and a titrant solution, where the sample is added to the vessel solution and is titrated with the titrant in order to determine the water content of the sample. The improved vessel solution is one containing an amine such a diethanolamine or imidazole, a reducing ion such as $SO_2$ alcohol, and iodide in an amount between 0.002 and 0.4 mol/liter. The titrant is an iodine-containing solution.

7 Claims, No Drawings

KARL FISCHER REAGENT AND ITS USE

TECHNICAL FIELD

This invention relates to Karl Fischer type reagents for the determination of water in samples, and more particularly to an improved reagent of the two-part type wherein problems such as false end-points and inaccurate results are eliminated.

BACKGROUND ART

The determination of moisture in materials such as liquids and solids by the Karl Fischer reaction is well known and widely used since it was first described by Karl Fischer in Angewandte Chemie 48, pages 394–396 (1935). Numerous publications have also described this technique for water determination, and reference is made to a general text by J. Mitchell, Jr. and D. M. Smith, entitled "Aquametry", published by John Wiley & Sons, 1980.

In the Karl Fischer reaction, a sample containing water is introduced into a vessel solution where it is readily absorbed. The vessel solution may be an anhydrous reagent containing sulfur dioxide, a buffer, and an anhydrous solvent, such as methanol, formamide, methyl cellosolve (a trademark of Union Carbide Co.), or mixtures thereof. A "titrant" containing iodine is introduced into the vessel solution containing the sample to be analyzed and produces a reaction of the type $H_2O + SO_2 + I_2 = 2HI + SO_3$.

In this Karl Fischer reaction, the water to be determined reacts with iodine on a quantitative basis; consequently, the amount of reacted iodine is a measure of the amount of water present in the sample. The titrant is generally a methanolic solution of iodine and is introduced into the vessel containing the sample and the vessel solution until no more iodine is used up. That is, an end point of the reaction is reached. Since the iodine is introduced via the titrant, the amount of titrant used is a measure of the amount of water in the sample to be tested.

Many different types of Karl Fischer reagents are commercially available and in use. For example, my U.S. Pat. No. 4,354,853 describes several of these Karl Fischer reagents, and particularly describes an advantageous "two-part" system, which is the subject of that patent application. These two parts are the titrant and the vessel solution. The titrant is essentially an iodine solution, while the vessel solution contains an alcoholic solvent, a reducing ion such as sulfur dioxide, and a buffer. A wide variety of buffers are described in that patent and in U.S. Pat. No. 4,378,972. Many of these buffers are amines. In U.S. Pat. No. 4,378,972, numerous "one-part" systems (containing all components-iodine, sulfur dioxide, and buffer-in one part) are described, as are several "two-part" systems (separate vessel solution and titrant.)

The present invention is related to improved two-part systems for the Karl Fischer determination of water in a sample. Many two-part systems appropriate for use in the present invention are described in my aforementioned U.S. Pat. No. 4,354,853, and in U.S. Pat. No. 4,378,972.

In a typical two-part system, also called a bicomponent system, part 1 of the system is the titrant. This is a solution of iodine in a solvent, for example the types of solvents described in U.S. Pat. No. 4,354,853. Part 11 of this bicomponent system is termed the vessel solution, and is usually a solution of sulfur dioxide and amine in an alcoholic solvent. The titration is carried out in a conventional titration apparatus. The titrant (iodine solution) is added to the vessel solution to modify it (pre-titration) until a certain slight excess of iodine is obtained, as indicated by suitable electrodes of the apparatus. The sample to be analyzed for water content is then added to the vessel solution and the iodine solution (titrant) is again titrated into the vessel solution until a slight excess of iodine is achieved. Accordingly, a substantial excess of iodine is not present until the titration end-point is reached. The volume of iodine solution added is a measure of the water content.

In the course of my experiments, I have found that certain vessel solutions give slow and inaccurate results if they consist only of amine, sulfur dioxide, and alcohol. The results become accurate only when a certain amount of iodide is present in the vessel solution. The following example illustrates this type of problem:

EXAMPLE I

A vessel solution consists of 0.9 moles of diethanolamine and 0.9 moles of sulfur dioxide in one liter of ethylene glycol monomethylether. The solution to be used as the titrant is a solution of 5/18 mole of iodine dissolved in xylene. This solution is used to measure the water content of an acetone solution with a known water content of 1.00%. When the titration is accomplished, the result is 1.06 %, which is an inaccurately high result.

Accordingly, it is an object of the present invention to provide an improved Karl Fischer reagent which will provide accurate results when used as a two-part system.

It is another object of the present invention to provide an improved Karl Fischer type of titration using an improved vessel solution, and in which accurate results are obtained without extensive calibration.

In addition to the problem of inaccurate results described hereinabove, it has been found in other laboratory experiments that the end-point of the initial titration was not reached quickly. As is known in this art, it is advantageous to quickly establish a "true" end-point for the titration. Present titrations proceed slowly toward the end-point of titration when very little water is left in the vessel. In this situation, the rate at which iodine is consumed is slow. Due to this slow reaction, an excess of iodine may appear even though small amounts of water are still present in the sample. This is called a "false" endpoint. After some time, usually a few seconds, the iodine has reacted with water and some more iodine titrant has to be added. Some more false end points may appear until the "true" end-point is reached. The true end point (i.e., the end-point indicating that all water in the sample has reacted with the iodine) will hold for a long time. Most Present procedures specify a time of 20 or 30 seconds for the end-point to hold, in order to determine a true end-point.

This slow reaction time leading to false end-points is not only an inconvenience, but is also a factor which may lead to some error. A prolonged titration gives the iodine a chance to be consumed via side reactions, i.e., reactions with species other than water. The problem of false end-points has been recognized in the art and is, for example, addressed for coulometric titrations in my U.S. Pat. No. 3,682,783. An example of this problem of false end-points is the following:

EXAMPLE II

A solution of 0.9 moles diethanolamine and 0.9 moles sulfur dioxide in one liter of anhydrous methanol is used as a vessel solution. The actual amount of the vessel solution placed in the titration vessel was 50 ml. The vessel solution is titrated with a water-free methanol solution that contains 5/18 moles of iodine per liter. The initial titration produces two false end-points, until the true end-point is reached.

Accordingly, it is another object of the present invention to provide an improved two-part Karl Fischer reagent and system in which the problem of false end-points is solved.

It is another object of this invention to provide an improved Karl Fischer reagent of the two-part type and a process for using said improved reagent to determine the water content of a sample, where the first end-point reached is the true end-point.

It has been found that certain two-part Karl Fischer systems in which the vessel solution is initially free of iodine and iodide suffer the disadvantages described in the preceeding Examples I and II. For example, vessel solutions containing alcohol, sulfur dioxide, and an amine selected from the group consisting of diethanolamine and imidazole are particularly subject to these aforementioned problems. Accordingly, when the vessel solutions are initially prepared I have found it advantageous to add small amounts of iodide to these vessel solutions before starting any titrations. The amount of iodide added is at least equal to 0.002 moles per liter, while the titrant is any iodine solution, including those described in U.S. Pat. No. 4,354,853. Thus, the invention specifically relates to two-part Karl Fischer reagents. As will be described hereinafter, the use of such improved vessel solutions leads to precisely accurate results without the problem of false end-points.

It should be noted that in the present practice of the art the vessel solution will always contain iodide in the course of carrying out successive titrations. However, the initial titration, when the vessel solution contains little or no iodide, is usually inaccurate. This will adversely affect the sample titration, as will be detailed in the following discussion.

In the present practice of the art, a certain volume, usually 20–50 ml, of the vessel solution is transferred from a storage vessel into a titration vessel. The next step is the so-called "pre-titration" in which the iodine-containing solution is added to the vessel solution until the end-point is reached. The purpose of the pre-titration is to remove all traces of water present in the vessel solution. After completion of the pre-titration, the sample is added and actual titration is carried out.

I have found that inaccuracies may also occur in the pre-titration steps due to the occurrence of false end-points as described above. If a false end-point is taken as the true end-point, the vessel solution is not properly prepared and the subsequent titration of a sample will be inaccurate.

Furthermore, the procedure presently followed in the art leads to another problem. The amount of iodide generated during pre-titration depends on the water content of the vessel solution, which may vary greatly depending on conditions of manufacture and storage after manufacture. Therefore, during pre-titration of a dry vessel solution, very little iodide is generated while a wet vessel solution requires the generation of higher amounts of iodide. I have found that this variability also leads to inaccuracies. It is not enough that a wet vessel solution be provided in order to obtain a certain amount of iodide in the vessel solution. This is an impractical solution because it is costly both in instrument time and in the amount of expensive titrant that would be consumed in a lengthy pre-titration.

Accordingly, it is a further object of the present invention to provide improved vessel solutions in two-part Karl Fischer reagents, where the vessel solutions initially contain a small amount of iodide.

It is a still further object of the present invention to provide improved vessel solutions for use in two-part Karl Fischer reagents and processes, where the step of pre-titration will not produce inaccuracies or false end-points.

DISCLOSURE OF INVENTION

This invention relates to improved Karl Fischer reagents of the two-part type wherein one part is the vessel solution in which the sample to be tested is placed, while the other part is the titrant which is combined with the vessel solution-sample combination in order to determine the amount of water in the sample. In contrast with other vessel solutions used in two-part Karl Fischer reactions, the present vessel solutions contain a small amount of iodide when initially manufactured. These vessel solutions can be taken directly from a large storage container and used for sample titrations without inaccuracies. Further, pre-titration with these improved vessel solutions is rapid and accurate, in contrast with the often lengthy and inaccurate pre-titration steps of the prior art.

It has been found that the aforementioned problems can be eliminated in vessel solutions containing an alcohol solvent, a reducing ion such as $SO_2$, and an amine buffer which is typically an amine, by adding a certain amount of iodide to the vessel solution. This iodide can be added in many ways known to those of skill in the art, the most convenient way being to add iodine and letting it react with water according to the Karl Fischer reaction.

The water can be deliberately added during manufacture of the vessel solution, or may be present if certain components of the vessel solution have a high affinity for water. The amount of added iodide per liter in the manufactured vessel solution is at least equal to or greater than 0.002 mole per liter, up to an amount not in excess of approximately 0.4 moles per liter. The titrant solution can be any solution of iodine, including those titrant solutions using the nonhydroscopic solvents of aformentioned U.S. Pat. No. 4,354,853.

Experimentation has led to the discovery that amine-based vessel solutions used in two-part Karl Fischer reagents will suffer from the problems described hereinabove. In particular, diethanolamine and imidazole based vessel solutions are significantly aided by the presence of iodide therein and form a unique group of vessel solutions in accordance with the present invention. However, the invention also extends, but in a less significant manner, to all other amine-based vessel solutions, including, but not limited to, diethylamine, propylamine, ethanolamine, triethanolamine, isopropylamine, and piperidine.

In a Karl Fischer process to determine the water content of a sample using the improved Karl Fischer reagent of this invention, the following steps are employed: an improved vessel solution containing initial amounts of iodide is taken in a measured amount from a large storage container and placed into a reaction titration vessel. A titration is then carried out using the titrant solution. Accurate results without delay or false end-points are obtained.

These and other objects, features, and advantages will be apparent from the following more particular description of the preferred embodiments.

BEST MODE FOR CARRYING OUT THE INVENTION

This invention specifically relates to two-component Karl Fischer reagents and processes using these improved reagents to determine the water content of a sample. Any titrant solution can be used in the practice of this invention, while the vessel solutions are selected to be particular vessel solutions that provide improved accuracy and rapid, true end-points. In general terms, these vessel solutions contain a reducing ion such as sulfur dioxide, alcohol, an amine, and a small amount of iodide. The amount of iodide per liter in the final vessel solution is at least 0.002 mole/liter, and can be as high as about 0.4 mole/liter.

This invention pertains only to two-part Karl Fischer reagents and processes using these two-part systems. The titrant solution can be any iodine solution, including those where the solvent is nonhydroscopic. The titrant solutions of U.S. Pat. No. 4,354,853 are particularly suitable.

The vessel solutions suitable for use in the present invention include those which use amines as buffers in solutions containing $SO_2$, alcohol, and iodide. Amine solutions that greatly benefit from the present invention and which are critical embodiments thereof are those which contain diethanolamine or imidazole. Other vessel solutions which are aided by the presence of iodide include those having the following amine buffers: diethylamine, ethanolamine, propylamine, triethanolamine, isopropylamine, and piperidine.

In a Karl Fischer process for determining the water content of a sample, these improved vessel solutions are useable directly from the storage containers in which they are shipped after manufacture. Accordingly, a desired amount of the vessel solution is removed from the storage container and placed into a reaction vessel. A titration is then carried out, using the titrant solution. No calibration steps are required prior to adding the sample, and accurate results having true end-points are immediately achieved.

In the introduction portion of this specification, two examples were given wherein known vessel solutions used in two-part systems were tested and found to give inaccurate results and/or false end-points.

In the experiment of Example I, a vessel solution was comprised of diethanolamine, sulfur dioxide, and ethylene glycol monomethyl ether. The titrant solution was iodine dissolved in xylene. When used to measure the water content of an acetone solution having a known water content, an inaccurately high result was obtained.

To illustrate the advantages of the present invention, this experiment was repeated using an improved vessel solution in accordance with the present invention. The vessel solution consisted of 0.9 moles of diethanolamine and 0.9 moles sulfur dioxide, in one liter of ethylene glycol monomethyl ether. The titrant was a solution of 5/18 moles of iodine dissolved in xylene to make one liter of final solution. However, before the actual titration to measure the water content of the acetone, a 50 ml volume of the vessel solution was treated with 0.005 moles of water, which is equivalent to 90 mg. of water. Then, an equal molar amount of 0.005 moles of iodine was also added to the vessel solution. The added water and iodine react according to the Karl Fischer reaction, forming iodide as a reaction product. When the determination of the water content of the acetone system is now carried out, the titration yields the correct result rather than an inaccurately high result.

This experiment was repeated but with imidazole replacing diethanolamine. The addition of iodine in the same amount, again yielded significantly more accurate results.

In the experiment of Example II described in the introduction to the specification, two false end-points were produced before the true end-point was reached, using a vessel solution containing 0.9 moles diethanolamine and 0.9 moles of sulfur dioxide in one liter of anhydrous methanol. The titrant solution contained 5/18 moles of iodine per liter in a solution consisting of iodine and water-free methanol.

In contrast with the false end-points obtained using the vessel solution and titrant described in the previous paragraph, this experiment was repeated using an improved vessel solution. The vessel solution is identical to that used in Example II, except that 0.002 moles of water and 0.002 moles of iodine are added to the 50 ml of vessel solution which was used for the titration. Using the same titrant solution and performing the same titration step, the first end-point which is reached is the true end-point.

From the foregoing examples, it is readily apparent that the presence of small amounts of iodide in the vessel solution will provide significantly improved results. In the course of my experiments I have found that certain two-part Karl Fischer systems, where the vessel solution is initially free of iodide, suffer the disadvantages described hereinabove. These disadvantages occur regardless of whether the titrant solution is a solution of iodine in alcohol (such as methanol, ethyl alcohol, ethylene glycol monomethyl ether, or other alcohol solvents), or in the nonhydroscopic solvents described in my U.S. Pat. No. 4,354,853. Thus, these problems arise in the amine-based vessel solutions of prior two-part Karl Fischer systems. In order to overcome these problems, in a preferred operation, the vessel solution is prepared by combining an amine, sulfur dioxide, alcohol, iodine, and a small amount of water. The amounts of water and iodine are always about equal, so that no free iodine, or only very small amounts of free iodine (preferrably less than 0.01 moles per liter), are present in the final vessel solution. After manufacture, this solution is stored until it is needed. It is then transferred in the required volume into the titration vessel where a single pre-titration step will provide a true end-point. The actual sample titration is carried out by forward titration, i.e., by adding the iodine titrant solution from the titration apparatus.

It has been discovered that, for the presence of iodide to be effective, at least 0.002 moles of iodide per liter have to be present in the vessel solution. Most or all of the added iodine will be present as iodide in the solution, since it reacts with water according to the above-described Karl Fischer reaction. The vessel solution of these improved two-part systems will not be subject to error and slow results. For many vessel solutions, for example those containing methanol, small amounts of water may be present even without the deliberate addition of water. While these small amounts may be suitable in the practice of the present invention, an additional small amount of water in accordance with the principles of the present invention can be added, together with the added iodine. As long as water is present in the vessel solution, any iodine added to the solution will be immediately reacted to form iodide. Only when all of the water is reacted will the iodine be stable in the solution. It is preferrable that almost all, or all, of the water be reacted.

While the invention has been described with respect to selected embodiments thereof and is particularly advantageous with diethanolamine and imidazole vessel solutions, it will be apparent to those of skill in the art that variations can be made therein without departing from the spirit and scope of the present invention. In this regard, additional components can be added to the vessel solution, or the amounts of the various components can be changed over wide ranges without departing from the principles of this invention. Still further, while sulfur dioxide is a suitable reducing agent in the Karl Fischer process, other reducing agents, such as methylsulfite, can be used.

In the practice of this invention, the term "vessel solution" is meant to be that solution which is provided by the manufacturer or distributor, and which is generally stored or shipped in a large container, prior to transfer of a measured amount into a titration apparatus. This "vessel solution", when made in accordance with the principles of this invention, can be used immediately for accurate titrations.

Having thus described my invention, what I claim as new and desire to secure by Letters Patent is:

1. A process for determining the water content of a sample using a two-component Karl Fischer reagent including a vessel solution and a titrant containing iodine comprising the steps of:
   transferring from a storage container to a reaction vessel a measured amount of vessel solution containing an amine, a reducing ion, alcohol, and iodide in an amount between about 0.002 and about 0.4 mole/liter, said vessel solution being substantially iodine-free,
   adding said sample vessel solution, and
   titrating said vessel solution in a forward direction with said iodine containing titrant to produce a Karl Fischer type reaction until a final titration end-point is reached, the amount of titrant consumed in said reaction being related to the amount of water in said sample, there being substantially no excess of iodine present in said process until said titration end-point is reached.

2. The process of claim 1, where said amine is selected from the group consisting of diethanolamine and imidazole.

3. The process of claim 1, where said amine is selected from the group consisting of diethylamine, ethanolamine, propylamine, triethanolamine, isopropylamine, an piperidine.

4. A process for determining the water content of a sample using a two-component Karl Fischer reagent including a vessel solution and a titrant containing iodine comprising the steps of:
   transferring from a storage container to a reaction vessel a measured amount of vessel solution containing an amine, a reducing ion, alcohol, and iodide in an amount between about 0.002 and about 0.4 mole/liter, said vessel solution being substantially iodine-free,
   pre-titrating said vessel solution in a forward direction to a true endpoint in one step by adding said iodine-containing titrant; said iodine being consumed by water in said vessel solution, there being substantially no iodine present after said pre-titration step,
   adding said sample to said pre-titrated vessel solution, and
   titrating said sample-containing vessel solution in a forward direction with said iodine titrant to produce a Karl Fischer type reaction until a final titration endpoint is reached, the amount of titrant being consumed in said reaction being related to the amount of water in said sample, there being substantially no excess iodine present in said process until said final titration endpoint is reached.

5. The process of claim 4, where said amine is selected from the group consisting of diethanolamine and imidazole.

6. The process of claim 4, where said vessel solution, prior to said pretitrating step, contains free iodine in an amount less than about 0.01 mole per liter.

7. The method of claim 4, where said titrant contains iodine in a non-hydroscopic solvent.

* * * * *